United States Patent [19]
Akiyama et al.

[11] Patent Number: 4,746,214
[45] Date of Patent: May 24, 1988

[54] SPECTROPHOTOMETER

[75] Inventors: Osamu Akiyama; Seiji Goto, both of Kyoto, Japan

[73] Assignee: Shimadzu Corporation, Japan

[21] Appl. No.: 910,383

[22] Filed: Sep. 22, 1986

[30] Foreign Application Priority Data

Sep. 30, 1985 [JP] Japan .................................. 60-218775

[51] Int. Cl.$^4$ ................................................ G01J 3/42
[52] U.S. Cl. ..................................... 356/325; 250/228; 356/236
[58] Field of Search ................ 356/319, 320, 323, 324, 356/325, 236; 250/228

[56] References Cited

U.S. PATENT DOCUMENTS

| | | | |
|---|---|---|---|
| 2,992,588 | 7/1961 | Henderson | 356/236 |
| 4,540,281 | 9/1985 | Akiyama | 356/236 |
| 4,575,252 | 3/1986 | Akiyama | 250/228 |
| 4,583,860 | 4/1986 | Butner | 356/236 |

Primary Examiner—F. L. Evans
Attorney, Agent, or Firm—Franklin D. Wolffe; Morris Fidelman

[57] ABSTRACT

A spectrophotometer provided with a plurality of integrating spheres of different types which can be selectively and exchangeably used in accordance with the type of a sample to be measured and the purpose of the measurement.

8 Claims, 4 Drawing Sheets

SPECTROPHOTOMETER

BACKGROUND OF THE INVENTION

This invention relates to a spectrophotometer provided with a plurality of integrating spheres which can selectively be used for different kinds of measurements.

For spectrophotometric measurement by using an integrating sphere, it has been customary to put an attachment including an integrating sphere in the sample chamber of a spectrophotometer. In particular, the attachment including an integrating sphere is provided as an accessory to a spectrophotometer, and the integrating sphere is fixed to the base of the attachment.

When a measurement is to be conducted with a spectrophotometer having an integrating sphere set in the sample chamber of the instrument, it is advisable to provide a plurality of integrating spheres of different types for selective use so as to make it possible to change the position of the integrating sphere in the sample chamber, the relative positions of the inlet and outlet windows of the integrating sphere, the number of the windows, and other factors in accordance with the kind and/or shape of a sample as well as the purpose of the measurement.

The conventional arrangement that the integrating sphere is fixed to the attachment base involves a problem that the user of the spectrophotometer must purchase various types of attachments for selective use in accordance with the type of a sample to be measured and the purpose of the measurement.

SUMMARY OF THE INVENTION

Accordingly, the primary object of the invention is to provide a spectrophotometer provided with a single attachment of the integrating sphere type, which enables measurement of various types of samples for various purposes of measurement.

To this end, there are provided a plurality of different types of integrating spheres, among which the one that is the most suitable for measurement of a particular sample can be selected and detachably mounted on the attachment.

DESCRIPTION OF THE PREFERRED EMBODIMENTS

Figure 1:
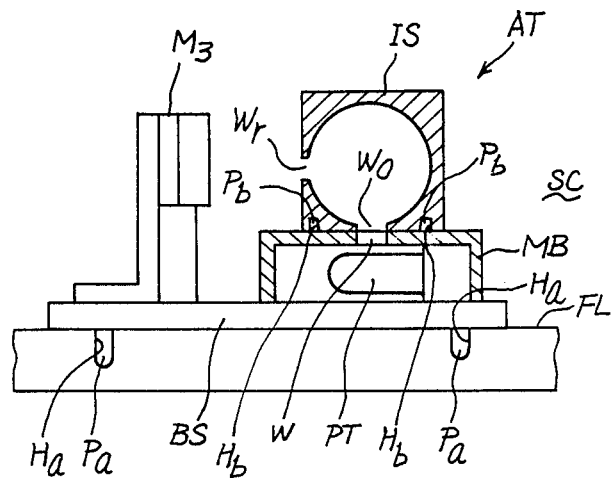
FIG. 1 is a schematic side view of an attachment constructed in accordance with the invention, with the integrating sphere shown in vertical section.
Figure 7:
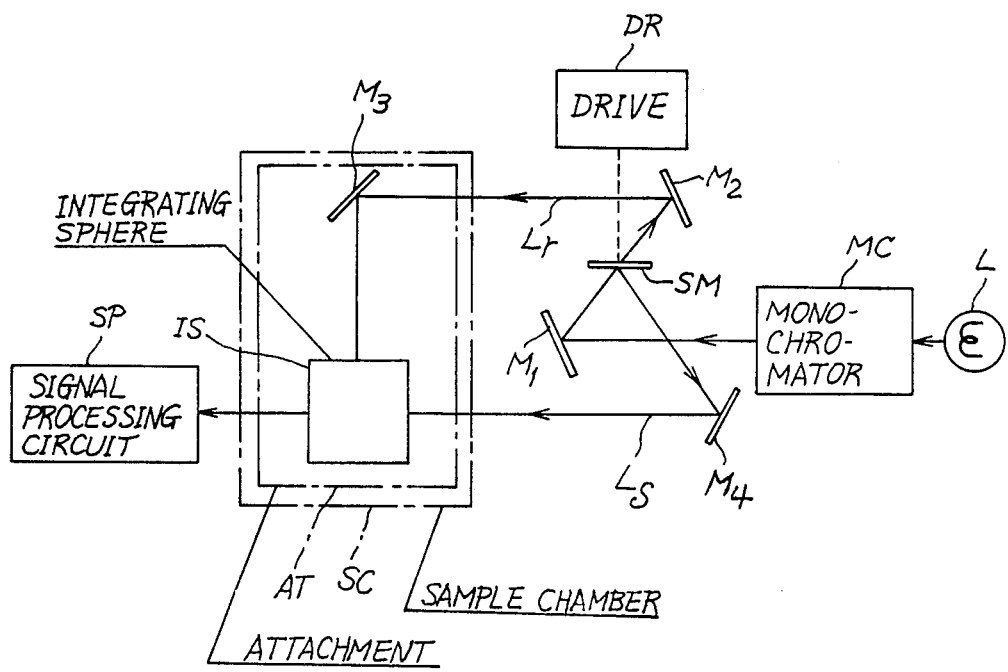
FIG. 7 is a schematic diagram of a double-beam spectrophotometer constructed in accordance with the invention.

Referring to FIG. 7 there is schematically shown a double-beam spectrophotometer provided with the attachment as shown in FIG. 1. A light source L emits a light beam over a range of measuring wavelengths. A monochromator MC receives the light beam and produces a monochromatic light of a selected wavelength, which is reflected by a mirror $M_1$ toward a rotatable sector mirror SM driven by a suitable drive DR. As the sector mirror SM is rotated, it splits the monochromatic light beam into two beams Lr and Ls.

The light beam Lr is reflected by a mirror $M_2$ so as to enter a sample chamber SC in which an attachment AT is set in a manner to be described later, while the other light beam Ls is reflected by a mirror $M_4$ so as to enter the sample chamber SC alternately with the beam Lr. The light beam Lr will be referred to as the reference beam and the light beam Ls, as the sample beam.

The attachment includes an integrating sphere and a photodetector as will be described hereinbelow, and the reference and sample light beams alternately enter the integrating sphere and the light emerging from the integrating sphere causes the photodetector to produce an electrical output signal, which is applied to a signal processing circuit SP.

FIG. 1 schematically shows an example of the attachment AT used in the instrument of FIG. 7. The attachment AT comprises a base BS provided on the under surface thereof with a plurality, say, two pins Pa downwardly projecting. The pins Pa are inserted into corresponding holes Ha formed in the floor FL of the sample chamber SC of the spectrophotometer thereby to set the attachment AT at a predetermined position in the chamber. A mounting box MB is fixed to the upper surface of the base BS and contains a photomultiplier tube PT. The box MB is formed in the upper wall thereof with a window W facing the photosensitive surface of the photomultiplier tube PT. An integrating sphere IS is mounted on the upper wall of the mounting box MB at such a position that the light emerging from the integrating sphere passes through the window W to impinge on the photosensitive surface of the photomultiplier tube PT and in such a manner that the integrating sphere can be dismounted from on the box MB for exchange for an integrating sphere of a different type.

Figure 2:
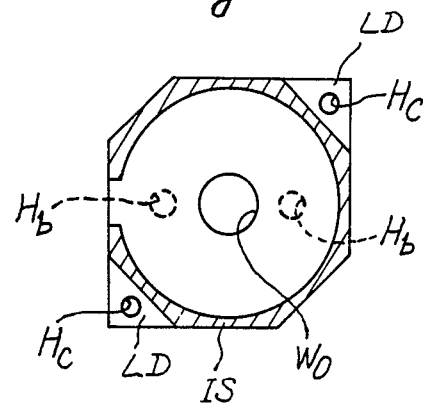
FIG. 2 is a schematic view, in transverse section, of the integrating sphere shown in FIG. 1.

A mirror $M_3$ is mounted on the base for directing the reference light beam Lr into the integrating sphere IS. The integrating sphere IS comprises a hollow cubic body which is chamfered at two diagonally opposite corners as seen from above as shown in FIG. 2, with the bottom portions of the corners left to form a flange-like ledge LD, in which a small hole Hc is formed.

On the top wall of the mounting box MB there are provided a pair of upwardly projecting positioning pins Pb, which engage in a corresponding pair of holes Hb formed in the bottom wall of the cubic body of the integrating sphere IS thereby to position the sphere in place on the mounting box MB.

A screw is passed through the hole Hc of each of the ledges LD to secure the integrating sphere IS to the top wall of the mounting box MB.

FIGS. 3 through 6 show different types of integrating spheres designed for use in a double-beam spectrophotometer.

Figure 3:
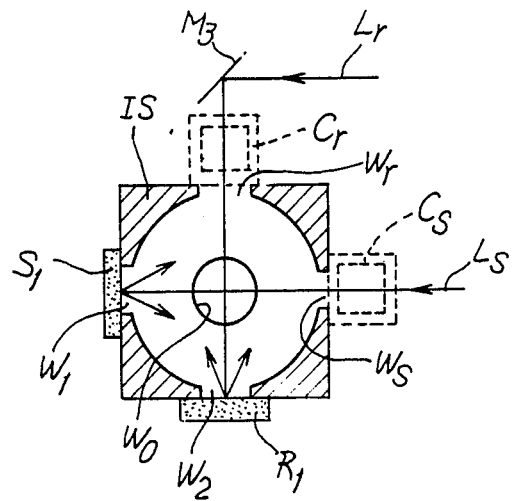
FIG. 3 through FIG. 6 are views similar to FIG. 2 but showing different types of integrating spheres.

FIG. 3 shows an integrating sphere of a standard type. The sphere is provided with a first inlet window Wr through which the reference light beam Lr is introduced into the integrating sphere IS and a second inlet window $W_s$ through which the sample light beam $L_s$ is introduced into the integrating sphere perpendicularly to the reference light beam Lr. The integrating sphere is also provided with another pair of windows $W_1$ and $W_2$ diametrically opposite to the above-mentioned windows Ws and Wr, respectively. The integrating sphere is further provided in the bottom wall thereof with an outlet window $W_o$, which coincides with the previously mentioned window W in the top wall of the mounting box MB, and through which the light emerges from inside the sphere. A sample $S_1$ the reflectance of which is to be measured is detachably set in the window $W_1$, and a light diffusing white plate $R_1$ to be used as a reference or standard is set in the window $W_2$.

With the sample $S_1$ and the reference $R_1$ set in the above-mentioned manner, the sample and reference light beams Ls and Lr impinge perpendicularly on the sample and the reference, respectively, so that only the diffuse reflection component of the light reflected from the sample can be measured.

For measurement of the transmittance of a sample, a pair of cells Cs and Cr containing the sample and a reference, respectively, are set in the windows Ws and Wr, respectively, just outside the integrating sphere IS as shown in phantom in FIG. 3. At this time, the windows $W_1$ and $W_2$ are closed by a standard white plate.

With the integrating sphere IS shown in FIG. 3, the specular reflection component of the light reflected perpendicularly from the sample $S_1$ goes out of the integrating sphere through the window Ws so as not to be measured, so that only the diffuse reflection component is measured. The arrangement is not suitable for measurement of the total reflected light from the sample including both the specular reflection and diffuse reflection components.

Figure 4:
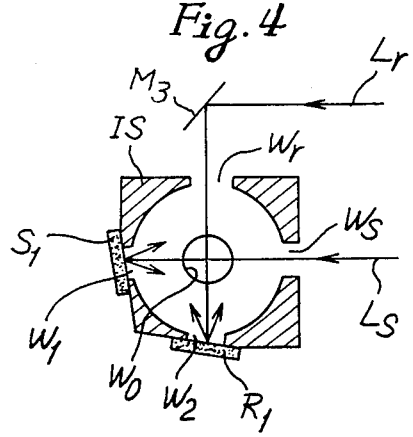

FIG. 4 shows an integrating sphere suitable for measurement of the total reflected light. In this sphere the windows $W_1$ and $W_2$ are so arranged with respect to the optical axes of the reference and sample light beams entering the integrating sphere through the inlet windows Wr and Ws that the sample $S_1$ and the reference $R_1$ set in the respective windows lie aslant relative to the reference and sample beams Lr and Ls impinging thereon.

Figure 5:
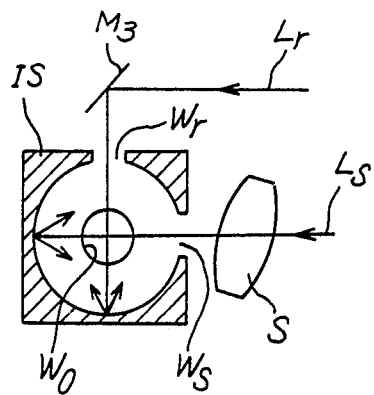

FIG. 5 shows an integrating sphere suitable for measuring the transmittance of light through a sample S of a given shape, such as a lens, a curved transparent plate, or the transmittance of light passing aslant through a thick transparent plate. The integrating sphere of this embodiment has no windows corresponding to the windows $W_1$ and $W_2$ in the sphere of FIG. 3.

Even if the windows $W_1$ and $W_2$ of the integrating sphere of FIG. 3 are closed by a standard white plate, it is impossible to measure the transmittance of a sample with a high degree of accuracy because the reflection characteristic of the white plate is not strictly identical to that of the inner surface of the integrating sphere. With the integrating sphere of FIG. 5, however, it is possible to measure the transmittance of a sample of a given shape with a high degree of accuracy and precision.

Figure 6:
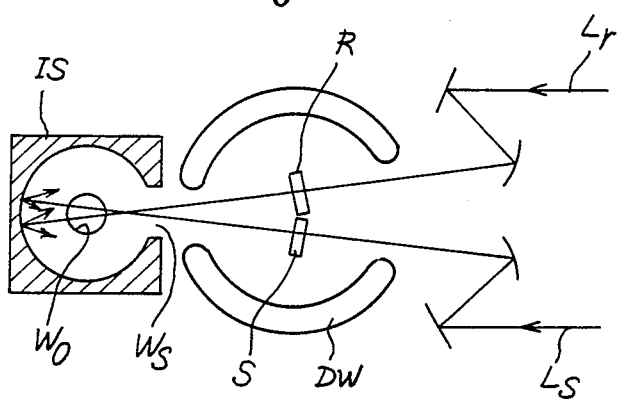

FIG. 6 shows an integrating sphere provided with only one inlet window Ws and one outlet window Wo. Before the inlet window Ws there are arranged side by side a reference R and a sample S, through which a sample light beam Ls and a reference light beam Lr pass so as to enter the integrating sphere IS through the common inlet window Ws. Since an integrating sphere preferably has as small a number of windows as possible, it is advantageous to have an integrating sphere of this type. In FIG. 6, the transmittance of the sample S is measured at the temperature of liquid nitrogen. A Dewar vessel schematically shown at DW keeps both the sample S and the reference R frozen to the state that they have lost transparency. The reference is frozen water, which functions as a light diffusing white plate.

In accordance with the invention, since the attachment is provided with a plurality of integrating spheres of different types for selective use, it is possible to conduct various types of measurements with the single attachment, with a resulting decrease in the cost of the instrument, and with less labor and yet a higher degree of accuracy and precision than if various types of measurements are made with difficulty with separate attachments including an integrating sphere.

What we claim is:

1. A spectrophotometer comprising:
   a light source for emitting a beam of light over a range of wavelengths;
   a monochromator for receiving said light to produce monochromatic light of a selected wavelength;
   a sample chamber;
   an attachment removably set in said sample chamber;
   a plurality of integrating spheres of different types;
   means for fixing a selected one of said integrating spheres to said attachment detachably so as to be exchanged for a different one of said integrating spheres;
   optical means for directing said monochromatic light into said selected integrating sphere; and
   means for measuring the light emerging from said selected integrating sphere.

2. The spectrophotometer of claim 1, wherein said optical means includes a beam splitter for splitting said monochromatic light emerging from said monochromator into a sample and a reference beam, and mirrors for directing said sample and reference beams into said selected integrating sphere.

3. The spectrophotometer of claim 1, wherein said fixing means comprises at least two upwardly projecting pins provided on said attachment and at least two holes formed in the bottom of the body of each of said integrating spheres to receive said pins thereby to fix said selected one of said integrating spheres on said attachment at such a position that said monochromatic light enters said integrating sphere.

4. The spectrophotometer of claim 2, wherein one of said integrating spheres is provided with a first pair of windows through which said sample and reference beams enter said integrating sphere; a second pair of windows which are diametrically opposite to said first pair of windows, and in which a sample and a reference are detachably set so that said sample and reference beams entering through said first pair of windows, respectively, impinge on said sample and reference; and an outlet window through which light from inside said integrating sphere goes out.

5. The spectrophotometer of claim 2, wherein one of said integrating spheres is provided with a first pair of windows through which said sample and reference beams enter said integrating sphere; a second pair of windows which are diametrically opposite to said first pair of windows, wherein said second pair of windows are closed by a white plate, and further comprising means for supporting a sample and a reference in said sample and reference light beams just outside said first pair of windows, respectively.

6. The spectrophotometer of claim 4, wherein another of said plurality of integrating spheres is provided with a single pair of windows through which said sample and reference beams enter said integrating sphere, and an outlet window through which light goes out from inside said integrating sphere, and including means for supporting a sample in said sample light beam outside said integrating sphere so that said sample beam passes through said sample.

7. The spectrophotometer of claim 2, wherein a third one of said integrating spheres is provided with: a first pair of windows through which said sample and reference beams enter said integrating sphere; a second pair of windows which are diametrically opposite to said first pair of windows, and in which a sample and a reference are detachably set so that said sample and reference beams entering through said first pair of windows, respectively, impinge aslant on said sample and reference; and an outlet window through which light from inside said integrating sphere goes out.

8. The spectrophotometer of claim 2, wherein a fourth one of said integrating spheres is provided with a single inlet window through which said sample and reference beams enter said integrating sphere at different angles, and an outlet window through which light goes out from inside said integrating sphere, and including means for supporting a sample and a reference in said sample and reference beams, respectively, outside said integrating sphere.

* * * * *